United States Patent
Quan et al.

(10) Patent No.: US 11,219,581 B2
(45) Date of Patent: Jan. 11, 2022

(54) NANOEMULSIONS WITH NEUTRALIZED FATTY ACID AND A METHOD PRODUCING THE SAME

(71) Applicant: Conopco, Inc., Englewood Cliffs, NJ (US)

(72) Inventors: Congling Quan, Woodbridge, CT (US); Gabriella Satchi Olivia Frey, Milford, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 96 days.

(21) Appl. No.: 16/652,406

(22) PCT Filed: Sep. 19, 2018

(86) PCT No.: PCT/EP2018/075315
§ 371 (c)(1),
(2) Date: Mar. 30, 2020

(87) PCT Pub. No.: WO2019/072507
PCT Pub. Date: Apr. 18, 2019

(65) Prior Publication Data
US 2020/0289383 A1    Sep. 17, 2020

(30) Foreign Application Priority Data
Oct. 10, 2017    (EP) .................... 17195794

(51) Int. Cl.
| *A61K 8/06* | (2006.01) |
| *A61K 8/36* | (2006.01) |
| *A61K 8/92* | (2006.01) |
| *A61Q 17/04* | (2006.01) |

(52) U.S. Cl.
CPC .............. *A61K 8/062* (2013.01); *A61K 8/361* (2013.01); *A61K 8/922* (2013.01); *A61Q 17/04* (2013.01); *A61K 2800/21* (2013.01)

(58) Field of Classification Search
None
See application file for complete search history.

(56) References Cited

U.S. PATENT DOCUMENTS

| 7,008,638 B2 | 7/2006 | Huglin et al. |
| 7,381,423 B2 | 3/2008 | Huglin et al. |
| 8,431,620 B2 | 4/2013 | Del Gaudio et al. |
| 8,388,985 B2 | 5/2013 | Leser et al. |
| 8,513,311 B2 | 8/2013 | Sagalowicz et al. |
| 2002/0106390 A1 | 8/2002 | Huglin et al. |
| 2005/0191330 A1 | 9/2005 | Huglin et al. |
| 2008/0255247 A1 | 10/2008 | Sagalowicz et al. |
| 2008/0311211 A1 | 12/2008 | Leser et al. |
| 2009/0118380 A1 | 5/2009 | Del Gaudio et al. |
| 2011/0177144 A1 | 7/2011 | Tashiro et al. |
| 2012/0177708 A1 | 7/2012 | Leser et al. |
| 2013/0189210 A1 | 7/2013 | Kinai |
| 2013/0209527 A1 | 8/2013 | Del Gaudio et al. |
| 2016/0120794 A1 | 5/2016 | Liu et al. |
| 2016/0215238 A1 | 7/2016 | Vetter et al. |
| 2017/0112764 A1 | 4/2017 | Wu |

FOREIGN PATENT DOCUMENTS

| CN | 101721930 | 6/2010 |
| CN | 201799243 | 4/2011 |
| CN | 102755847 | 10/2012 |
| CN | 104874305 | 9/2015 |
| CN | 105148758 | 12/2015 |
| EP | 2952194 A1 | 12/2015 |
| JP | 201656111 | 4/2016 |
| WO | WO02080864 | 10/2002 |
| WO | WO2005110370 | 11/2005 |
| WO | WO2015066777 | 5/2015 |
| WO | WO2015152420 | 10/2015 |

OTHER PUBLICATIONS

Search Report and Written Opinion in EP17195794; dated Mar. 21, 2018.
Search Report and Written Opinion in PCTEP2018075315; dated Nov. 12, 2018.

*Primary Examiner* — Nannette Holloman
(74) *Attorney, Agent, or Firm* — Edward A. Squillante, Jr.

(57) ABSTRACT

The method for making a nanoemulsion is described. The method uses a neutralized fatty acid and does not require traditional surfactant in order to yield stable nanoemulsion having a diameter from 70 to 550 nm.

18 Claims, No Drawings

NANOEMULSIONS WITH NEUTRALIZED FATTY ACID AND A METHOD PRODUCING THE SAME

FIELD OF THE INVENTION

The present invention is directed to a nanoemulsion comprising neutralized fatty acid, optionally, water miscible liquid, and a method for making the same. More particularly, the invention is directed to a nanoemulsion that is prepared from oil, water and neutralized fatty acid. Surprisingly, the nanoemulsion may be prepared via an energy efficient process and can be made without high pressure processing steps when water miscible liquid is included.

BACKGROUND OF THE INVENTION

Nanoemulsions are becoming increasingly popular for use in personal care compositions. They are stable and have a high surface area in view of their unit volume.

Nanoemulsions can also carry actives in their water and oil phases and are desirable since they enhance penetration of actives through the skin as well as topical benefits delivered to consumers that employ end use compositions formulated with the same. Nanoemulsions not only result in better active penetration, but they also improve the therapeutic impact and overall sensory benefits appreciated by consumers when compared to compositions formulated without them.

A downside to formulating with nanoemulsions concerns the high pressure processing steps required to make them. Typically, conventional mixing followed by multiple runs of high pressure homogenization are required to make a nanoemulsion. The equipment can be expensive, and the process is time consuming and uses an abundance of energy.

It is of increasing interest to develop nanoemulsions that result in excellent benefits to consumers after topical application. This invention, therefore, is directed to nanoemulsions comprising oil, water and neutralized fatty acid. The nanoemulsions may surprisingly be prepared via an energy efficient process and they may be prepared without high pressure processing steps when water miscible liquid, like glycerol, is included in the water phase of the emulsion. The resulting nanoemulsions made by the process of this invention are unexpectedly stable and suitable for use in skin care and wash compositions. Such nanoemulsions can be made without requiring the use of any traditional emulsification (or surfactant) system other than what is provided for by the neutralized fatty acids used.

Additional Information

Efforts have been disclosed for making nanoemulsions. In U.S. Published Patent Application No. 201710112764A1, nanoemulsions having reversible continuous and dispersed phases are described.

Even other efforts have been disclosed for making nanoemulsions. In Chinese Published Patent Applications CN1051418758A and CN104874305A, methods for preparing nanoemulsions are described.

Still other efforts have been disclosed for making nanoemulsions. In WO 15066777A1, nanoemulsions having fatty alcohols are described.

None of the additional information above describes a nanoemulsion and method for making a nanoemulsion as set forth in the present claims.

SUMMARY OF THE INVENTION

In a first aspect, the present invention is directed to a method for making an oil-in-water nanoemulsion comprising the steps of combining:

(a) oil as an internal phase;
(b) water as an aqueous phase; and
(c) a fatty phase comprising C8 to C22 neutralized fatty acid, neutralized fatty acid and a neutralizer, fatty acid and neutralizer, or a combination thereof, the phases being mixed to produce a macroemulsion and when the water miscible liquid is not used, the macroemulsion is homogenized in a single pass at a process pressure of 600 to 7000 psi to produce a nanoemulsion having a particle size from 70 to 550 nm, wherein 10 to 100% of the fatty acid is neutralized.

In a second aspect, the present invention is directed to the nanoemulsion made by the process described in the first aspect of the invention.

In a third aspect, the present invention is directed to an end use composition comprising the nanoemulsion described in the second aspect of the invention.

In a fourth aspect, the present invention is directed to a method for enhancing the performance of an end use composition by combining the composition with the nanoemulsion in the first aspect of the invention.

All other aspects of the present invention will more readily become apparent from the description and examples which follow.

Skin, as used herein, is meant to include skin on the arms (including underarms), face, feet, neck, chest, hands, legs, buttocks and scalp (including hair). Diameter, as it relates to the macro- and nanoemulsions, means the volume average diameter D[4,3] of the oil droplets in microns or nanometers. Oil droplet size may be measured with a commercially available Malvern Mastersizer. End use composition (water or oil continuous but preferably water continuous) is a composition for topical application and includes a cream, lotion, balm, serum, gel, mousse, aerosol, deodorant, antiperspirant, shampoo, conditioner, make-up and personal wash, including bars and liquids. Such an end use composition can be the nanoemulsion of this invention or nanoemulsion added to an end use composition. Traditional surfactant, as used herein, means a surfactant other than the neutralized fatty acid used. Benefit active is an oil soluble component that delivers a benefit to skin after being topically applied. Oil, as used herein, is meant to include a substance that has a melting point below 75° C., including oils which are benefit actives like sunscreens. High pressure, as defined herein, means 600 psi or more, and preferably, over 850 psi. In a preferred embodiment, the end use composition is water continuous as is the nanoemulsion of this invention. In another preferred embodiment, the end use composition of this invention is a leave-on skin lotion or cream, or a solid or liquid personal wash composition.

Unless explicitly stated otherwise, all ranges described herein are meant to include all ranges subsumed therein. The term comprising is meant to encompass the terms consisting essentially of and consisting of. For the avoidance of doubt, a nanoemulsion of this invention comprising oil, water, neutralized fatty acid and glycerol is meant to include a nanoemulsion consisting essentially of the same and a nanoemulsion consisting of the same. Except in the operating comparative examples, or where otherwise explicitly indicated, all numbers in this description indicating amounts or ratios of materials or conditions and/or physical properties of materials and/or use are to be understood as modified by the word "about".

DETAILED DESCRIPTION OF THE INVENTION

The only limitation with respect to the oil that may be used in the nanoemulsion of the present invention is that the same is suitable for topical use.

Illustrative examples of the oils that may be used in this invention include triglycerides (animal and/or vegetable) like soybean oil, sunflower oil, coconut oil, palm kernel oil, castor oil, rapeseed oil, palm oil, grape seed oil, shea butter, cocoa butter, caprylic/capric triglyceride, safflower oil, fish oil, mixtures thereof or the like.

Other oils suitable for use include mineral oil, jajoba oil, isoparaffins, a $C_{12}$-$C_{15}$ alkyl benzoates, polyalphaolefins, isohexadecane, silicone oils, siliconized waxes like siliconized beeswax, vegetable wax, petrolatum, mixtures thereof (including with those oils above) or the like. Soybean and sunflower oil are the most preferred triglyceride oils. Petrolatum is also preferred for use with or without other oils.

When petrolatum is used, the same typically has a melting point range from 25° to 65° C. Examples of such petrolatum are jellies like Vaseline® petroleum jelly made commercially available from Unilever, White Petroleum USP from Calumet Penreco as well as Petrolatum G2212 and White Protopet® from Sonneborn.

Within the nanoemulsion, oil typically makes up from 40% to 80%, and preferably, from 45% to 75%, and most preferably, from 50 to 65% by weight of the nanoemulsion, including all ranges subsumed therein.

An optional ingredient which may be used in the oil phase of the present invention is an oil phase stabilizer. For example, small amounts (0.01 to 2%, preferably 0.1-1% by weight of the nanoemulsion) of antioxidant may be used. When the oil used is triglyceride, a preferred antioxidant which may be used is butylated hydroxytoluene (BHT).

As to the $C_8$ to $C_{22}$ fatty acids used with the oils described herein, the same may be branched or linear, saturated or unsaturated. Caprylic, lauric, myristic, palmitic, stearic and/or behenic acid are often preferred saturated linear fatty acids. Preferred branched fatty acids include isostearic acid, isopalmitic acid, 17-methylstearic acid and/or 15-methylpalmitic acid.

The unsaturated fatty acids suitable for use preferably include palmitoleic acid, oleic acid, petroselinic acid, linoleic acid, erucic acid, nervonic acid and/or conjugated linoleic acid. It is within the scope of the present invention to utilize a mixture of the aforementioned fatty acids. In an especially preferred embodiment, longer chain fatty acids like stearic acid, isostearic acid or mixtures thereof are used in the nanoemulsions of the present invention when the end use composition is a leave-on care composition. Shorter chain fatty acids like lauric and/or myristic acid are preferred when the end use composition is a wash off composition.

Typically fatty acid makes up from 2 to 20%, and preferably, from 3 to 18%, and most preferably, from 4 to 15% by weight of the nanoemulsion, including all ranges subsumed therein. In an especially preferred embodiment, the weight ratio of fatty acid to oil in the nanoemulsion is from 1:20 to 1:3, and preferably, 1:15 to 1:4, and most preferably, from 1:12 to 1:5, including all ratios subsumed therein.

It is within the scope of the present invention to optionally include, within the oils, and/or fatty acids, oil soluble benefit actives like 12-hydroxystearic acid, (including an ester thereof) vitamins A, D, E or K, vitamin E acetate, sunscreens like octocrylene, octisalate (ethylhexyl salicylate), homosalate (3,3,5-trimethylcyclohexyl salicylate) ethylhexylmethoxycinnamate, 2-ethylhexyl-2-hydroxybenzoate or drometriazole trisiloxane. Other oil soluble benefit actives suitable for use include resorcinols like 4-ethyl resorcinol, 4-hexyl resorcinol, 4-isopropyl resorcinol as well as 5-substituted resorcinols like 4-isopropyl-5-methylbenzone-1,3-diol or 4-cyclohexyl-5-methyylbenzone-1,3-diol.

Even other oil soluble actives suitable for use include omega-3 fatty acids, omega-6 fatty acids, climbazole, farnesol, ursolic acid, myristic acid, geranyl geraniol, hexanoyl sphingosine, terpineol, thymol, and mixtures of such aforementioned benefit actives.

In an especially preferred embodiment, the oil soluble benefit active used in this invention is a retinoic acid precursor represented by the formula:

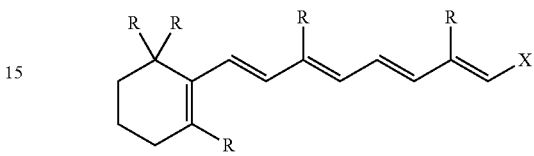

where each R is independently a hydrogen or a $C_{1-6}$ alkyl group and X is

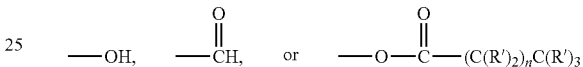

and further where each R' is hydrogen or a $C_1$-$C_3$ alkyl and n is an integer from 0 to 16 (preferably, 1 to 5).

Preferably, the retinoic acid precursor is retinol, retinal, retinyl propionate, retinyl palmitate, retinyl acetate or a mixture thereof. The often most desired retinoic acid precursor used is retinyl proponate, retinyl palmitate or a mixture thereof, with or without climbazole.

When used, the oil soluble benefit agent typically makes up from about 0.001 to 12%, and preferably, from 0.01 to 8%, and most preferably, from 0.1 to 6% by weight of the nanoemulsion, including all ranges subsumed therein.

Neutralizer suitable for use to neutralize the fatty acid in the nanoemulsion of the present invention is limited to the extent that the same may be used in a topical composition and is able to neutralize up to 100% by weight of the fatty acid within the nanoemulsion. Preferred neutralizers suitable for use include NaOH, KOH, triethanolamine or mixtures thereof. It is within the scope of the present invention to add, with or in lieu of fatty acid and neutralizer, fatty acid soap, and fatty acid soap with additional neutralizer.

As to the amount of neutralizer employed to make the nanoemulsions of the present invention, the same is adjusted so that from 10 to 100%, and preferably, from 20 to 85%, and most preferably, 35 to 65% by weight of all fatty acid within the nanoemulsion is neutralized. To the extent neutralization of the fatty acid exceeds 70%, it is especially preferred that less than 55%, and most preferably, less than 50% by weight of the total neutralizer used is NaOH when the fatty acid used is saturated, linear and $C_{16}$ or greater.

In another preferred embodiment, if fatty acid neutralization is to exceed 70% with NaOH as the neutralizer, it is preferred that more than 45%, and preferably, more than 50% by weight of the fatty acid used to make the nanoemulsion is branched and saturated, and/or linear and unsaturated.

Optionally traditional anionic and amphoteric surfactants may be used when preparing the nanoemulsion of the present invention. However, it has been unexpectedly discovered that traditional surfactants other than what is provided for by the neutralized fatty acid is not needed to make the stable nanoemulsion of the present invention. Therefore, in the present invention, the nanoemulsion will comprise less than 6% by weight, and preferably, from 0.001 to 4% by weight, and most preferably, no traditional surfactant in addition to the neutralized fatty acid used.

If used, optional anionic surfactants which may be used include sodium acyl isethionate, sodium acyl methyl isethionate, sodium methyl cocoyl taurate, sodium trideceth sulphate, sodium lauryl ether sulfate-3EO, acylglutamate, acylglycinate, lauroyl sarcosinate, acyl sarcosinate or mixtures thereof. Optional amphoteric surfactants suitable for use such include coco betaine, cocamidopropyl betaine, sodium lauroamphoacetate, lauramidopropyl hydroxysultaine, cocamidopropyl hydroxysultaine or mixtures thereof.

In a preferred embodiment a water miscible liquid is not used in the aqueous phase. Preferably, water makes up at least 25%, by weight, of the aqueous phase, preferably at least 50%, even more preferably at least 75% of the aqueous phase, by weight of the aqueous phase.

In a preferred embodiment, the aqueous phase comprises water and a water miscible liquid. Preferably, the water miscible liquid makes up from 25 to 75% by weight of the aqueous phase.

As to the aqueous phase (water or water and water miscible liquid mixed therewith), the same typically makes up from 15 to 55%, and preferably, from 25 to 45%, and most preferably, from 30 to 40% by weight of the nanoemulsion.

Preferred water miscible liquids suitable for use in the present invention include those classified as humectants like glycerol, sorbitol, hydroxypropyl sorbitol, hexyleneglycol, 1,3-butylene glycol, 1,2,6-hexanetriol, ethoxylated glycerine, propoxylated glycerine or mixtures thereof.

In a preferred embodiment, the water miscible liquid used is glycerol. Typically the water miscible liquid to water weight ratio is from 1:3 to 3:1, and preferably, 1:2.5 to 2.5:1, and most preferably, 1.5:1 to 1:1.5, including all ratios subsumed therein.

It is within the scope of the present invention to include water soluble actives within the aqueous phase of the nanoemulsion. Such water soluble actives are limited only to the extent that they can be used in topical compositions. Illustrative examples of the water soluble actives that may be used in this invention include niacinamide, picolinamide, ascorbic acid, salicylic acid, dihydroxyacetone, extracts, like pomegranate extract, vitamins, like Vitamin C, as well as sunscreens such as the salts of benzophenone-4 and phenylbenzimidazole sulfonic acid. Mixtures and water soluble derivatives of the same may also be used. Typically, when used in the nanoemulsion, water soluble active makes up from 0.0 to 6%, and preferably, from 0.001 to 5%, and most preferably, from 0.01 to 4%, based on total weight of the nanoemulsion and including all ranges subsumed therein.

When manufacturing the nanoemulsion of the present invention, ingredients are first mixed (i.e, oil phase to water phase, or water phase to oil phase or simultaneously) in a conventional mixing vessel equipped with a rotor/stator high shear device to produce a macroemulsion. The high shear mixing device used, which may be in line or within the mixing vessel, is commercially available from suppliers like ESCO-LABOR AG and Silverson®. The macroemulsion produced typically has a diameter from 0.8 to 8 microns, and preferably, 0.8 to 5 microns, and most preferably, 1.0 to 2 microns as measured with an art recognized Malvern Mastersizer. Rotor speed is often from 1,000 to 8,000 rpm, and preferably, from 2,000 to 7,500 rpm, and most preferably, from 3,000 to 7,000 rpm. The time required to homogeneously mix the ingredients is the time for a theoretical pass minimum, yielding the desired homogeneous macroemulsion.

Alternatively, the macroemulsion may be made in a continuous mode, by supplying oil phase and aqueous phase simultaneously into a low pressure homogenizer (e.g. low pressure sonolator, typically operating at 100 to less than 500 psi, made commercially available from Sonic Corporation of Connecticut, USA).

The macroemulsion prepared is then passed through a high pressure homogenizer to form the desired nanoemulsion of the present invention. The high pressure homogenizers suitable for use are the art recognized devices that may be operated at 600 to 7000 psi, and preferably, from 900 to 6000 psi, and most preferably, from 1000 to 5500 psi to produce the nanoemulsion of the present invention. Those made commercially available from BEE International, Massachusetts, USA (manufacturer of DeBee series homogenizers) and Sonic Corporation of Connecticut, USA (manufacturer of high pressure sonolators) are suitable for use.

Surprisingly, it has been discovered that one single pass of macroemulsion (prepared with neutralized fatty acid according to this invention and not requiring traditional surfactant) through a homogenizer will yield the desired nanoemulsion having a diameter from 70 to 550 nm, and preferably, from 80 to 475 nm, and most preferably, from 80 to 400 nm, including all ranges subsumed therein.

Additionally, it has been unexpectedly discovered that when water miscible liquid is included in the water (aqueous) phase, high pressure homogenization is not required to produce nanoemulsion of the aforementioned diameter sizes. Therefore, nanoemulsion of desired diameter is produced after mixing solely with a commercially available rotor/stator device (or low pressure homogenizer) under the conditions described above.

In a preferred embodiment, a water miscible liquid makes up from 25 to 75% by weight of the water miscible phase and the nanoemulsion is produced without homogenization that exceeds 500 psi.

In a preferred embodiment, an aqueous phase with water soluble components and an oil phase with oil soluble components are each first mixed and prepared prior to mixing all ingredients with a high shear mixing device. If a phase is unclear and/or not homogeneous, it is within the scope of the present invention to separately heat each phase to a temperature from 30 to 85° C., and preferably, from 40 to 80° C., and most preferably, from 45 to 75° C. until a homogeneous solution or mixture is obtained.

The pH of the resulting nanoemulsions is typically from 6 to 10, and preferably, from 6.5 to 8.5, including all ranges subsumed therein. In an often preferred embodiment, mixtures of fatty acids (e.g., lauric and myristic acid) are preferred.

The nanoemulsions made according to the present invention may be used as end use compositions, and therefore, applied topically to hair and/or skin directly by consumers. It is also within the scope of the present invention to add the nanoemulsion to a commercially available end use product to boost the efficacy of such end use product.

Since the nanoemulsions of the present invention are water continuous, it is preferred that the end use composition used with the nanoemulsion is also water continuous.

When nanoemulsion is not the end use composition, the consumer will be instructed to mix nanoemulsion and end use composition (leave-on or wash off) in his or her hands until a homogeneous mixture is made. Upon obtaining a homogeneous mixture, product may then be topically applied. In a most preferred embodiment and when nanoemulsion and end use composition are mixed, from 2 to 50%, and preferably, from 5 to 35%, and most preferably, from 10 to 25% by weight nanoemulsion is used based on total weight of nanoemulsion and end use composition, including all ranges subsumed therein.

Since water is present, traditional preservatives found in topical consumer products may be used. The preservatives typically make up from 0.01 to 3% by weight of the nanoemulsion. Illustrative examples of the preservatives suitable for use include iodopropynyl butyl carbamate, phenoxyethanol, 1,2-alkane diols, hydroxyacetophenone, ethylhexylglycerine, hexylene glycol, methyl paraben, propyl paraben, benzyl alcohol or mixtures thereof. Often, a mixture of 1,2-octane diol and phenoxyethanol at a weight ratio of 4:6 to 6:4 is preferred. It should be understood that when water miscible liquid is used (e.g., at least 30% by weight of the aqueous phase), a reduction in nanoemulsion water activity is observed thereby resulting in less of a need for preservatives.

A wide variety of packaging may be employed to store and deliver the nanoemulsion of this invention. Packaging is often dependent upon the type of personal care end-use. For instance, leave-on skin lotions and creams, shampoos, conditioners and shower gels generally employ plastic containers with an opening at a dispensing end covered by a closure. Typical closures are screw-caps, nonaerosol pumps and flip-top hinged lids. Packaging for antiperspirants, deodorants and depilatories may involve a container with a roll-on ball on a dispensing end. Alternatively these types of personal care products may be delivered in a composition formulation in a container with a propel/repel mechanism. Metallic cans pressurized by a propellant and having a spray nozzle serve as packaging for antiperspirants, shave creams and other personal care products.

The Examples are provided to further illustrate the invention. They are not intended to limit the scope of the claims.

Examples 1-2

One Pass High Pressure Homogenization Examples (No Water Miscible Liquid)

Macroemulsions (diameter about 1-5 microns) were prepared in a one liter mixer equipped with a rotor/stator high shear device (commercially available from ESCO-LABOR AG, Switzerland). The aqueous phase ingredients were added to the mixer and heated with moderate stirring to 75° C. and until the contents were clear. The oil phase ingredients were combined and heated to 75° C. in a separate mixing vessel until a molten mixture was obtained. The oil phase was gradually added to the aqueous phase and mixed with the rotor/stator device (about 3000 rpm). When the addition of the oil phase was complete and the macroemulsion was formed in the mixer, the contents were transferred and passed through a Nano DeBEE homogenizer one single time (at 5000 psi) to obtain the desired nanoemulsions of the present invention and as depicted in Table I.

TABLE I

| | Examples | | | | | | | |
|---|---|---|---|---|---|---|---|---|
| | 1a | 1b | 1c | 1d | 2a | 2b | 2c | 2d |
| Ingredient Aqueous Phase | wt %** | | | | | | | |
| KOH (Neutralizer) | 25% | 50% | Percent of Neutralization 75% | 100% | — | — | — | — |
| NaOH (Neutralizer) | — | — | — | — | Percent of Neutralization 25% | 50% | 75% | 100% |
| DI Water | balance | | | | | | | |
| Preservative | <1 | | | | | | | |
| Oil Phase | | | | | | | | |
| White petrolatum USP | 50 | | | | | | | |
| Lauric acid | 8 | | | | | | | |
| D[4,3], nm* | 186 | 288 | 218 | 320 | 207 | 207 | 204 | 347 |

*Measured with a Malvern Mastisizer
**Weight percent based on total weight of the nanoemulsion As can be seen from the data, nanoemulsions, made consistent with this invention, may successfully be prepared with neutralized fatty acid as the sole emulsifiers, yielding oil droplet diameters of less than 350 nm after only (one) 1 pass through a high pressure homogenizer with pressure at 5000 psi.

Examples 3-7

Nanoemulsion Production without High Pressure Homogenization

Emulsions were prepared in a one liter ESCO mixer equipped with a scraper and rotor/stator high shear device (ESCO-LABOR AG, Switzerland). Added to the mixer was neutralizer, glycerol and water. The contents were mixed to uniformity while being heated to a temperature from about 55 to 75° C. Oil phase components were added to the aqueous mixture while heating continued or first melted in a separate container and then gradually added to the aqueous phase in the ESCO mixer. Agitation and intense mixing was achieved with the scraper and rotor/stator device. When the addition of all oil phase components was complete, the mixture was intensively mixed by the rotor/stator device at about 3000 RPM to 7000 RPM (rotor speed) for up to 5 minutes. The resulting nanoemulsion was cooled and recovered. Oil droplet size was measured with a Malvern Mastersizer.

TABLE II

| | Examples | | | | | | | | | |
|---|---|---|---|---|---|---|---|---|---|---|
| | 3a | 3b | 3c | 4a | 4b | 4c | 5 | Comp** | 6 | 7 |
| Ingredient Aqueous Phase | Wt %**** | | | | | | | | | |
| Triethanolamine (Neutralizer) | 20% | 50% | 80% | Percent of Neutralization — | — | — | — | — | — | — |
| KOH (Neutralizer) | — | — | — | 50% | Percent of Neutralization 50% | 80% | — | — | — | — |
| NaOH (Neutralizer) | — | — | — | — | — | — | Degree of Neutralization 50% | 80% | 80% | 80% |
| Glycerol | 15.64 | | | | | | | | | |
| DI Water | balance | | | | | | | | | |

TABLE II-continued

| | Examples | | | | | | | | | |
|---|---|---|---|---|---|---|---|---|---|---|
| | 3a | 3b | 3c | 4a | 4b | 4c | 5 | Comp** | 6 | 7 |
| Oil Phase | | | | | | | | | | |
| Petrolatum G2212 | | | | | | | 60 | | | |
| Stearic acid | 9 | 9 | 9 | 9 | — | 9 | 9 | 9 | — | — |
| Lauric acid | — | — | — | — | 6 | — | — | — | — | — |
| Myristic acid | — | — | — | — | 3 | — | — | — | — | — |
| Isostearic acid | — | — | — | — | — | — | — | — | 9 | — |
| Oleic acid | — | — | — | — | — | — | — | — | — | 9 |
| D[4,3], nm* | 317 | 192 | 130 | 352 | 156 | 363 | 338 | NA*** | 202 | 194 |

*Measured with a Malvern Mastersizer
**Comparative example 1
***Product not dispersable
****Weight percent based on total weight of the nanoemulsion.

The data in Table II demonstrates that when water miscible liquid, like glycerol, is included in the aqueous phase, nanoemulsions can surprisingly be produced without requiring high pressure homogenization. Moreover, the results demonstrate that NaOH as the sole neutralizer is not preferred when the fatty acid is saturated, linear and $C_{16}$ or greater with neutralization exceeding 70%.

Example 8

The emulsions in this Example were made in a manner similar to the one described for Examples 3-7.

TABLE III

| Examples Ingredient | Comp 2 wt %** | 8 wt %** |
|---|---|---|
| Aqueous Phase | | |
| Triethanolamine (Neutralizer) | Percent of Neutralization 50% | |
| Glycerol | 15.13 | 20.4 |
| DI Water | balance | Balance |
| Oil Phase | | |
| Petrolatum G2212 | 26.1 | 26.1 |
| Capric/Caprylic Triglyceride | 7.8 | 7.8 |
| Hydrogenated polydecene (Pionier 0030 SYN, H&R) | 2.6 | 2.6 |
| Lilac ™ C12-22 Alkane | 13.0 | 13.1 |
| Stearic acid | 10.4 | 10.4 |
| Glycol Stearate & Stearamide AMP | 3.9 | |
| Glyceryl Monostearate | 1.8 | |
| Cetyl Alcohol | 1.0 | |
| Propylparaben | 0.1 | |
| Octyldodecanol | 1.3 | |
| Dimethicone | 0.5 | |
| D[4,3], nm* | Phase Inversion | 282 |

*Measured with a Malvern Mastisizer
**Weight percent based on total weight of nanoemulsion.
***Comparative Example 2.

The results in Table III demonstrate that neutralized fatty acid alone is sufficient to produce a water continuous emulsion and that use of nonionic surfactant with the neutralized fatty acid is not required (and often not desired) as it can result in nanoemulsion phase inversion.

Example 9

Nanoemulsion with sunscreen as the oils were made in a manner similar to the one described in Examples 3-7 (mixing with a rotor/stator equipped mixer). Avobenzone, Octocrylene, ethylhexyl salicylate (Octisalate) and Homosalate were the sunscreens used in the oil phase. Alkyl (c12-c15) benzoate was the solvent used in oil phase.

TABLE IV

| INGREDIENT | wt %** |
|---|---|
| Aqueous phase | |
| Sodium Hydroxide (Neutralizer) | Percent of neutralization 50% |
| Glycerol | 20.7 |
| Deionized Water | Balance |
| Oil Phase | |
| Isostearic Acid | 7.6 |
| Avobenzone | 4.8 |
| Octocrylene | 12.4 |
| Octisalate | 13.8 |
| Homosalate | 8.3 |
| c12-c15 Alkyl benzoate | 11.1 |
| D[4,3], nm* | 453 |

*Measured with a Malvern Mastisizer
**Weight percent based on total weight of the nanoemulsion.

The results demonstrate that nanoemulsion consistent with this invention can surprisingly be made with sunscreen in the oil phase and in the absence of high pressure homogenization.

The invention claimed is:

1. A method for making an oil-in-water nanoemulsion, said method comprising the steps of mixing:
   (a) oil as an internal phase;
   (b) water as an aqueous phase; and
   (c) a fatty phase comprising $C_8$ to $C_{22}$ neutralized fatty acid, neutralized fatty acid and neutralizer, fatty acid and a neutralizer, or a combination thereof, the phases being mixed to produce a macroemulsion and the macroemulsion is homogenized in a single pass at a process pressure of 600 to 7000 psi to produce the nanoemulsion having a particle size from 70 to 550 nm, wherein 10 to 100% of the fatty acid is neutralized.

2. The method according to claim 1, wherein the oil is an animal and/or vegetable triglyceride.

3. The method according to claim 1, wherein the oil is soybean, sunflower, coconut, palm kernel, castor, rapeseed, palm, grape seed, safflower, fish oil or a mixture thereof.

4. The method according to claim 1, wherein the oil is shea butter, cocoa butter, mineral oil, jojoba, silicone oil or a mixture thereof.

5. The method according to claim 1, wherein the oil is siliconized wax, $C_{12}$-$C_{15}$ alkyl benzoate, polyalphaolefin, isohexadecane, beeswax, vegetable wax, petrolatum or a mixture thereof.

6. The method according to claim 1, wherein the oil is soybean oil, sunflower oil, petrolatum or a sunscreen.

7. The method according to claim 1, wherein the water makes up at least 25%, by weight of the aqueous phase.

8. The method according to claim 1, wherein the fatty acid is 20 to 75% neutralized.

9. The method according to claim 1, wherein the oil comprises oil soluble benefit active and water comprises water soluble active.

10. The method according to claim 1, wherein the macroemulsion is produced in a mixer with a rotor/stator or in a homogenizer at a pressure of 100 to 500 psi, the mixer with the rotor/stator having a rotor speed of 1000 to 8000 rpm.

11. The nanoemulsion obtainable by the method according to claim 1.

12. The method of claim 1, wherein a water miscible liquid is not used in the aqueous phase.

13. The method according to claim 7, wherein the water makes up at least 50% by weight of the aqueous phase.

14. The method according to claim 7, wherein the water makes up at least 75% by weight of the aqueous phase.

15. The method according to claim 1, wherein the fatty acid to oil is present at a weight ratio of 1:20 to 1:3 in the nanoemulsion.

16. A method for making an oil-in-water nanoemulsion, said method comprising the steps of mixing:
    (a) oil as an internal phase;
    (b) water and a water miscible liquid as an aqueous phase; and
    (c) a fatty phase comprising $C_8$ to $C_{22}$ neutralized fatty acid, neutralized fatty acid and neutralizer, fatty acid and a neutralizer, or a combination thereof, the phases being mixed to produce a macroemulsion and the nanoemulsion is produced after mixing the macroemulsion without homogenization that exceeds 500 psi to produce the nanoemulsion having a particle size from 70 to 550 nm,
    wherein 10 to 100% of the fatty acid is neutralized,
    and wherein the water miscible liquid makes up from 25 to 75% by weight of the aqueous phase.

17. The method according to claim 16, wherein the water miscible liquid comprises glycerol, and the nanoemulsion produced has an oil droplet size from 80 to 475 nm.

18. The method according to claim 16, wherein the water miscible liquid is glycerol and a glycerol to water weight ratio is 1:3 to 3:1 within the nanoemulsion.

* * * * *